United States Patent [19]

Barkley

[11] Patent Number: 4,602,634
[45] Date of Patent: Jul. 29, 1986

[54] METHOD AND INSTRUMENT FOR APPLYING A FASTENER TO A TISSUE USING MEANS TO GRASP, GUIDE AND PULL THE FASTENER THROUGH THE TISSUE

[75] Inventor: Andrew Barkley, Basking Ridge, N.J.

[73] Assignee: Ethicon, Inc., Somerville, N.J.

[21] Appl. No.: 726,856

[22] Filed: Apr. 24, 1985

Related U.S. Application Data

[63] Continuation-in-part of Ser. No. 535,110, Sep. 23, 1983, abandoned.

[51] Int. Cl.⁴ .............................................. A61B 17/10
[52] U.S. Cl. .......................... 128/334 C; 227/DIG. 1
[58] Field of Search .............. 128/334 R, 334 C, 335, 128/330; 227/DIG. 1

[56] References Cited

U.S. PATENT DOCUMENTS

| | | | |
|---|---|---|---|
| 4,121,591 | 10/1978 | Hayes | 128/330 |
| 4,281,657 | 8/1981 | Ritchey | 128/330 |
| 4,326,531 | 4/1982 | Shimonaka | 128/326 |

FOREIGN PATENT DOCUMENTS 1385691 12/1964 France .................................. 40/300

Primary Examiner—Michael H. Thaler
Attorney, Agent, or Firm—Robert L. Minier

[57] ABSTRACT

A method of joining tissue with a staple and a receiver. The staple is placed on one side of the tissue to be joined and the receiver on the opposite side of the tissue. The legs of the staple are grasped and/or guided as they penetrate the tissue and are retained by the receiver.

11 Claims, 7 Drawing Figures

METHOD AND INSTRUMENT FOR APPLYING A FASTENER TO A TISSUE USING MEANS TO GRASP, GUIDE AND PULL THE FASTENER THROUGH THE TISSUE

This is a continuation-in-part patent application of copending patent application Ser. No. 535,110, filed Sept. 23, 1983, now abandoned.

TECHNICAL FIELD

This invention relates, in general, to the fastening together of portions of tissue in surgical procedures.

BACKGROUND OF THE INVENTION

In various surgical procedures fasteners in the form of staples, and the like, are employed for holding tissue portions together to facilitate healing of a wound or incision. For example, a locking staple having a tongue and groove structure by which the staple is locked, is disclosed in U.S. Pat. No. 2,881,762. A metal staple, especially adapted for ligating blood vessels, is disclosed in U.S. Pat. No. 3,079,608. International Patent Application No. PCT/SU79/00049 discloses a variety of fastening devices and instruments for performing circular anastomosis on the large intestine. The aforementioned disclosures serve as examples for a wide variety of tissue fastening devices and techniques that may be employed in general and/or specific surgical situations.

One common type of fastening device for joining or holding together soft tissue portions is the generally U-shaped staple which is typically fabricated from suitable metals. Such staples, although generally described as having two legs joined by a link to define a U-shape when unclinched, may also be regarded as having a configuration of an open loop when unclinched. The legs need not be necessarily parallel but are typically adapted for penetrating the tissue portions and for receiving between them some of the tissue material.

Other examples of U-shaped or open loop staples as well as methods and instruments for applying said staples to tissue are disclosed in U.S. Pat. Nos. 3,252,643, 3,482,428, 3,692,224, 3,790,057, 3,795,034, 3,889,683, 4,198,982, 4,316,468 and 4,329,576.

Other tissue fastening devices have been proposed and differ from staples per se in that these other devices may have a plurality of components that do not have to be clinched in the manner of a metal staple. One such device is disclosed in U.S. Pat. No. 4,060,089 and includes a fastener strip provided with a plurality of longitudinally spaced parallel prongs which are adapted to penetrate overlapped tissue portions from one side so that the distal ends of the prongs project from the other side of the tissue portions.

The fastener device further includes a retainer strip which is adapted to be placed on the other side of the tissue portions opposite the fastener strip to engage the ends of the projecting fastener strip prongs and to secure the tissue portions tightly between the fastener strip and the retainer strip. The fastener strip prongs each include a plurality of spaced apart engaging members for engaging the retainer strip at the desired position relative to the prongs. This provides for the capability of adjusting the distance between the fastener strip and the retainer strip. Such a fastening device may be fabricated from a bio-degradable or absorbable material.

Other patents such as U.S. Pat. Nos. 2,286,578 and 3,638,654 disclose instruments for applying flexible sutures with needles that are inserted into the tissue portions.

Other types of fasteners that include a fastening member with legs joined by a link and secured by a retaining receiver on one side of an incision are disclosed in U.S. Patent Application Ser. Nos. 506,088; 506,151; and 506,083 filed June 20, 1983 and assigned to the assignee of the instant application.

U.S. Pat. No. 4,006,747 discloses the application of a flexible fastener to tissue by means of a slotted hollow straight needle with a plunger for pushing the fastener through the needle. The application of a similar fastener in a non-surgical situation is disclosed in U.S. Pat. No. 4,215,807.

Also, in commonly assigned patent application Ser. No. 506,146 filed June 20, 1983 an instrument having a pair of spaced apart needles oriented in generally parallel planes is disclosed. Each needle has a distal end adapted for piercing the tissue portions. Each needle is hollow and has a passage extending along its length from a fastening member receiving opening to a discharge opening at the distal end of the needle. Each needle also has a slot extending along its length in communication with the passage and facing the slot of the other needle. According to the method of that patent application, the fastener is applied by first approximating tissue portions in generaly face-to-face relationship. The hollow needles are inserted through the approximated tissue portions to locate the receiving openings on one side of the wound or incision and to locate at least portions of the discharge openings on the other side of the wound or incision. The fastening member is placed with each of the legs disposed in one of the needle passages and with the link extending through the needle slots between the needles. The fastening member is urged along the needles to locate at least a portion of the link on one side of the incision adjacent to one of the tissue portions and locate a portion of each leg on the other side of the incision where it is restrained by a suitable receiver. The needles are withdrawn and the fastener remains holding the tissue together.

Although many of the above discussed types of tissue fastening devices and techniques are satisfactory in various applications, there is a need to provide an improved method for fastening mammalian tissue with reduced trauma. It would also be desirable to provide an improved fastening method for use with fasteners fabricated from absorbable materials that can provide primary approximation of the tissue edges to insure that the tissue edges will not lose contact. The improved method should insure that the staple legs, as they pass through the tissue, fully align with the openings in the receiver. The improved method should eliminate the possibility of misalignment of the staple legs with the openings in the receiver. When misalignment occurs, blind movement of the legs is required until an opening is met, very often causing undue trauma to the tissue. The method of the present invention accomplishes all the above desired objectives.

Furthermore, many of the biocompatible materials which are most suitable for use within the human body lack the necessary physical characteristics to allow the material to be used as a fastening device. Often these materials do not have the required physical properties to allow them to be molded or otherwise manufactured into a staple with legs sufficiently strong and/or rigid that the legs have enough strength to penetrate tissue without breaking or bending. It is a further object of the present invention to provide a method that can be used with staples made from virtually any biocompatible polymeric materials even those materials having minimum strength and/or rigidity.

When using a staple having two or more staple legs joined together at one end of the legs and trying to push the staple through tissue so the free ends of the staple legs will meet openings in a receiver and be interlocked therewith, very often the staple legs will either converge or diverge as a result of the compressive force placed on them as the staple is being pushed through the receiver causing the staple legs to misalign with the openings in the receiver. This phenomenon results in non-fastening of the staple with the receiver or causes undue trauma to the tissue, both highly undesirable results. The method of the present invention eliminates this problem.

Also, it would be desirable to provide a relatively simple yet effective and rapidly operating instrument for applying a variety of fasteners according to such an improved method.

SUMMARY OF THE INVENTION

A method and instrument for applying a fastener or a group of fasteners to close a wound or incision in mammalian tissue by holding together portions of the tissue defining the wound or incision so as to facilitate healing of the wound or incision. The method can be employed with a variety of types of fasteners comprising a fastening member having a pair of legs joined by a suitable link with that link lying against one of the tissue portions on one side of the wound and acting as a stop means. The fastener also includes a receiver having a pair of openings. The fastener is placed on the opposite side of the wound and retains the leg penetrating the tissue.

The method requires the use of an instrument having needles which, at their distal end, have means for guiding and/or grasping the legs of the fastening member or staple. The needles may be hollow or they may be solid at least up to the portion that guides and/or grasps the legs. The diameter of the needle must be such as to readily pass through the opening of the receiver which is going to accept the leg.

When applying a fastener according to the method of the present invention, two or more tissue portions are approximated in a generally face-to-face relationship. The staple portion of the fastener is disposed on one side of the tissue to be joined and the receiver portion of the fastener is spaced on the opposite side of the tissue to be joined. The instrument having the needles with the guiding and/or grasping means is placed so that the needles pass through the openings in the receiver and penetrate the tissue to guide and/or grasp the free end of the legs of the staple. The needles are removed through the opening in the receiver by reversing their motion. The legs of the staple are caused to follow the guiding and/or grasping needles and the legs of the staple penetrate the tissue. At least a portion of the legs of the staple are passed through the openings of the receiver. The staple legs are guided into the holes in the receiver and aligned therewith. The staple legs are engaged and retained by the receiver and the guiding and/or grasping means removed and the fastener remains holding together the tissue portions.

This method and instrument may be used for a variety of such types of fasteners. Numerous other features of this novel method and instrument will be apparent from the following detailed description and accompanying drawings.

BRIEF DESCRIPTION OF THE DRAWING

In the accompanying drawings, forming part of the specification, like numerals are employed to designate like parts throughout the same.

DETAILED DESCRIPTION OF THE DRAWINGS

Figure 1:
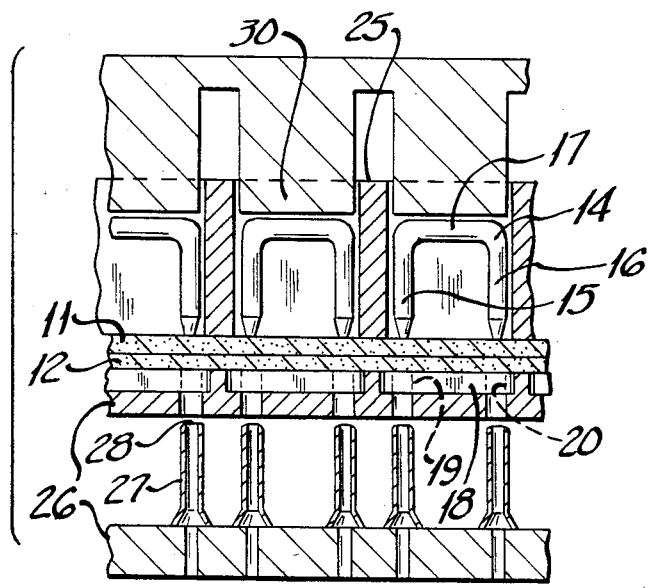
FIG. 1 is a cross-sectional view of one means for carrying out a method in accordance with the present invention (In this figure the means is in the fully opened position)
Figure 2:
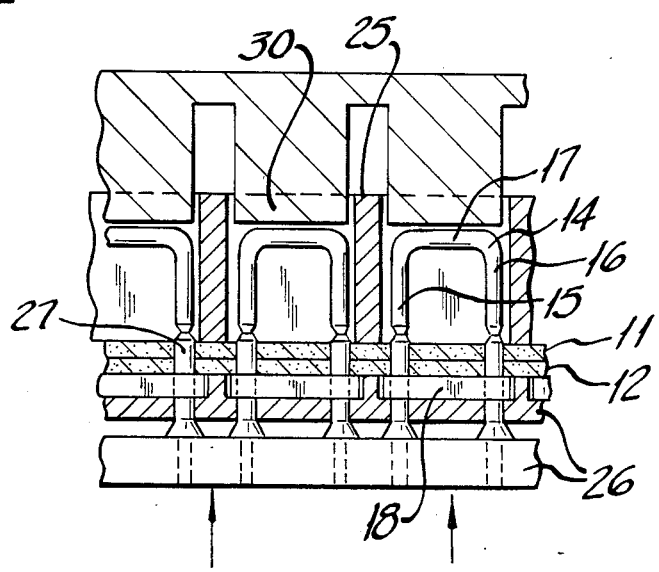
FIG. 2 is a view in elevation of the means depicted in FIG. 1 with the instrument in its first closed position.
Figure 3:
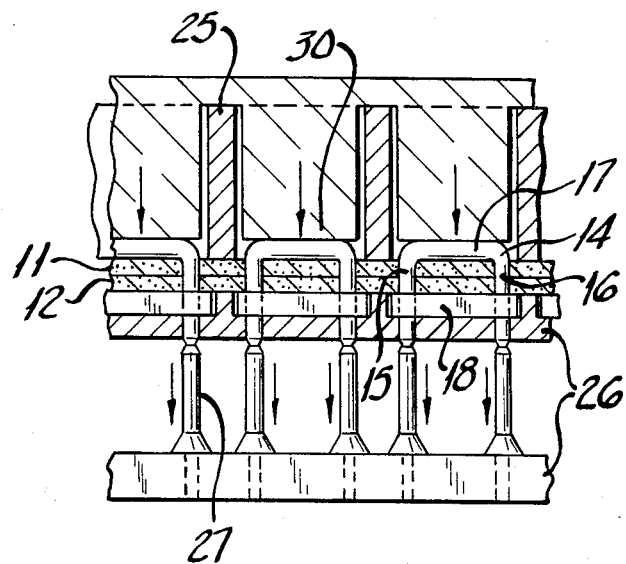
FIG. 3 is a view in elevation of the means depicted in FIG. 1 with the instrument in its second closed position.
Figure 4:
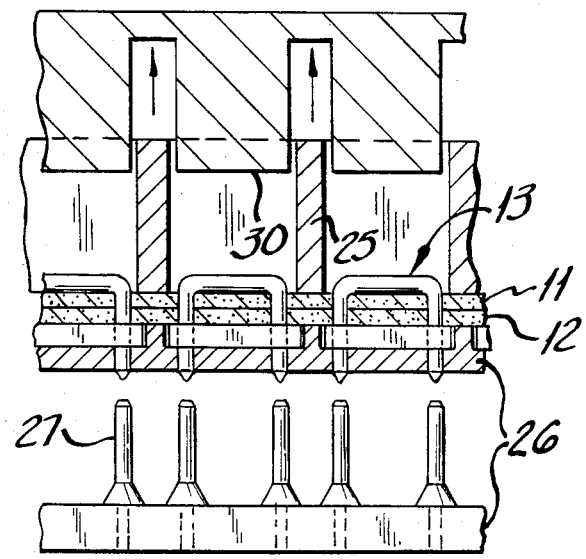
FIG. 4 is a view in elevation of the means depicted in FIG. 1 with the instrument in the open position and with the tissue fastening means in place.

In FIGS. 1 through 4 there is shown one means for carrying out the method of the present invention. In this embodiment two pieces of tissue 11 and 12 are being joined by a fastening member comprising a staple 14 having a pair of legs 15 and 16 which are generally parallel and connected by a cross piece 17. The fastening member includes a receiver 18 having a pair of holes or openings 19 and 20 for accepting the legs of the staple and locking therewith. As shown in FIG. 1 the staples are carried in one jaw 25 of an instrument and may be held in that jaw either by friction or some type of latch means (not shown for the sake of clarity). This jaw is placed on one side of the two pieces of tissue to be joined. A second jaw 26 of the instrument is placed on the opposite side of the two pieces of tissue to be joined. This jaw carries a plurality of the receivers with the openings in the receivers disposed directly in line with the legs of the staple. The second jaw includes guiding means 27 which is aligned with the openings or holes in the receivers. The free end of each staple leg is tapered and fits into the open end 28 of the guiding means. As shown in FIG. 2, the guiding means is inserted through the openings in the receivers through the tissue to be joined so that the open end of the guiding means 28 contacts the free end of each staple leg 15 and 16. At this point, if the staples are being held in the first jaw by a latch, the latch is released and a pusher means 30 is actuated to push the staple 14 and the guiding means 27 back down through the tissue forcing the legs of the staple into the holes of the receiver 18 to be retained thereby. This step is depicted in FIG. 3 of the drawings. At this point, the pusher is released and the guiding means may be removed leaving the fastening members in the tissue as depicted in FIG. 4.

Figure 5:
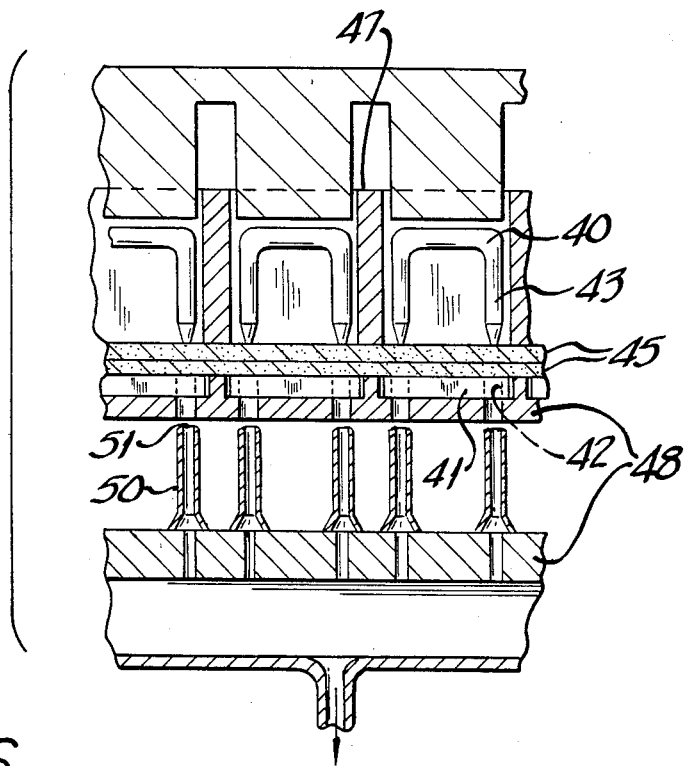
FIG. 5 is a cross-sectional view of another means for carrying out an alternate method of the present invention with the instrument in its initial open position.
Figure 6:
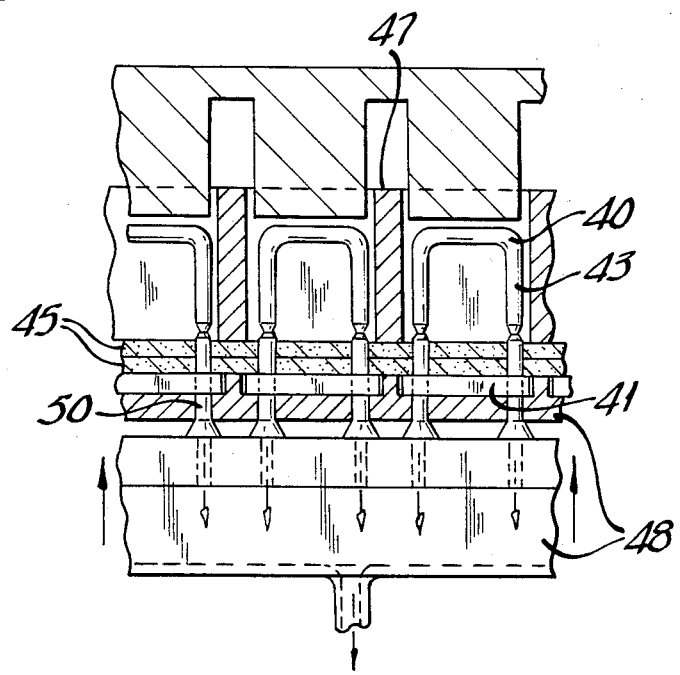
FIG. 6 is a view in elevation of the means depicted in FIG. 5 with the instrument in its closed position.
Figure 7:
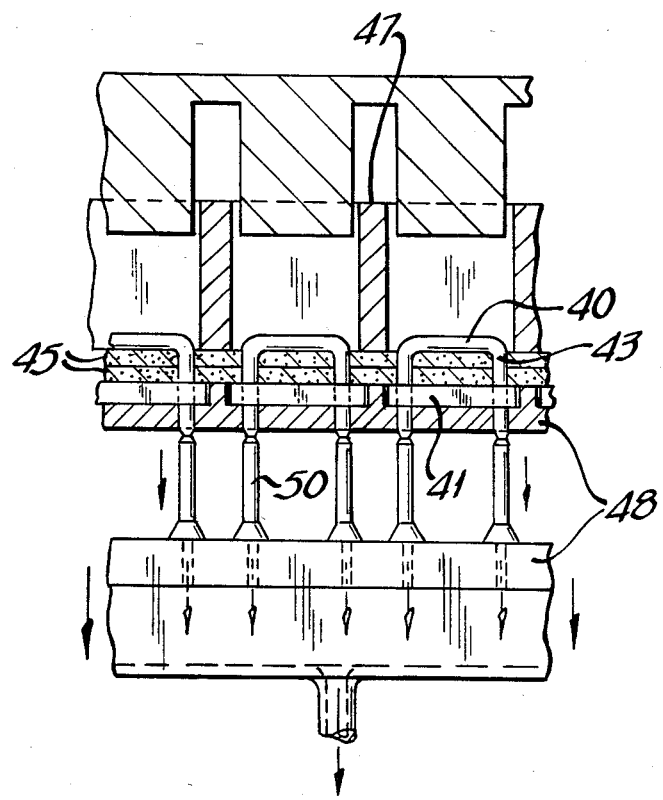
FIG. 7 is a view in elevation of the means depicted in FIGS. 5 and 6 of the instrument in its open position again and with the fastening means in place joining the tissue.

Referring to FIGS. 5, 6, and 7 there is shown another means for carrying out an alternative method of the present invention. Again, a two-legged staple 40 and an appropriate receiver 41 having openings 42 for retaining the legs 43 of the staple are disposed in opposite jaws 47 and 48 of an instrument and the opposite jaws placed on the opposite sides of the tissue 45 to be joined. The staples are held in spaces in the jaws by friction as are the receivers. The second jaw 48 includes grasping and guiding means 50 which are hollow. The free ends 51 of the hollow grasping and guiding means are aligned with the openings in the receiver. The free ends are sharpened to aid in tissue penetration. The opposite end of the grasping and guiding means is attached to appropriate suction. In operation, the guiding and grasping means are moved to pass through the openings in the receiver, penetrate the tissue, and contact the free ends of the legs of the staple as shown in FIG. 6. At this point, suction is applied to the opposite end of the grasping and guiding means and the means then returned to its original position as shown in FIG. 7. This operation pulls the staple along with the grasping and guiding means through the tissue into engagement with the receivers to be retained thereby. At this point, the suction may be removed and the jaws opened to release the tissue which is joined by the appropriately locked staple and receiver.

Though staples and receivers having a pair of legs and a complementary pair of openings have been described, it should be appreciated that the fasteners may have single legs or multiple legs and the receivers may have single openings or multiple openings or various combinations of the two. The receiver and the fastening member or staple, when in the final position, should be locked in place and this may be accomplished either by the receiver in some manner grasping on to the staple leg such as by an interference fit or by having means on the staple leg to retain the receiver such as barbed areas and the like as are well known in the art.

The staples or fastening members and receivers may be made from various biologically acceptable polymeric materials and these materials may be either of the absorbable type or the non-absorbable type. Suitable absorbable materials are made from the polymers and copolymers of the glycolides, lactides, polydioxanones and the like. Suitable non-absorbable products can be made from the polymers such as polyethylene, polypropylene, polyester, nylon and the like.

The staples and receivers of the fasteners of the present invention may be made from any of the biocompatible polymeric materials that can be molded or otherwise shaped with the desired form of staple and receiver. The strength and rigidity of the material used is no longer critical in the method of the present invention. If a relatively strong material is used an assist may be provided in placing the staple by pushing the staple through the tissue as it is being guided through the tissue while if a weak material is used for the staple the staple leg may be grasped and pulled through the tissue without any compressive or bending forces being placed on the staple legs.

Unexpectedly, the method of the present invention both insures that the staple leg will meet and join with the opening in the receiver while allowing the staple to be manufactured from any of the desired biocompatable polymeric materials.

The jaws of the means or instruments for applying fasteners may be joined or they may be separate. The jaws may carry one or virtually any number of fastening members and the other jaw may carry one or any number of receivers for those fastening members. The jaws may either have a shape such as to apply the staples in a straight line or in a circular configuration or in any other configuration or shape as desired. The instrument itself may be disposable or it may be of the reusable variety wherein cartridges carrying both the fastening members and the receivers may be placed in the reusable jaws as is well known in the art. The instrument and fasteners should be sterile and, hence, should be made of materials that are readily sterilizable by the well-known heat, radiation, ethylene-oxide, and similar means for sterilization.

From the foregoing, it will be observed that numerous variations and modifications may be effected without departing from the true spirit and scope of the novel concept of the invention. It is to be understood that no limitation with respect to the specific articles, instruments, and methods illustrated herein is intended or should be inferred. It is, of course, intended to cover, by the appended claims, all such modifications as fall within the scope of the claims.

What is claimed is:

1. A method of joining mammalian tissue using fasteners comprising a fastening member having a plurality of legs, said legs being joined together at one end of said legs and with the free ends of said legs adapted to pass through said tissue and a receiver having the same number of openings as there are fastening member legs, said openings being spaced apart the same distance that the legs are spaced apart so that each leg is in alignment with a receiver opening, for retaining said fastening member legs after the fastening member legs have passed through said tissue, said method comprising:

placing the fastening member on one side of the tissue to be joined and the receiver on the opposite side of the tissue to be joined;

penetrating said tissue through the openings in the receiver with means for engaging said fastening member leg to form openings in the tissue through which said fastening member legs may pass;

engaging said fastening member leg with said engaging means;

guiding said fastening member legs through the opening in the tissue to be joined using the engaging means;

and guiding said fastening member legs through the openings in said receiver to be retained thereby.

2. A method according to claim 1 wherein the fastening member is a U-shape staple and the receiver has a pair of openings for accepting and retaining the legs of the staple.

3. A method according to claim 1 wherein the means for engaging the fastening member leg is sharpened to assist in penetrating the tissue.

4. A method according to claim 1 or 2 including pushing the fastening member through the tissue while guiding the fastening member legs through the tissue.

5. A method of joining mammalian tissue using fasteners comprising a fastening member having a plurality of legs; said legs being joined together at one end of said legs and with the free ends of said legs adapted to pass through said tissue and a receiver having the same number of openings as there are fastening member legs, said openings being spaced apart the same distance that the legs are spaced apart so that each leg is in alignment with a receiver opening, for retaining said fastening member legs after the fastening member legs have passed through said tissue, said method comprising;

placing the fastening member on one side of the tissue to be joined and the receiver on the opposite side of the tissue to be joined;

passing a grasping and guiding means through the openings in the receiver;

penetrating said tissue with said grasping and guiding means passed through the openings in the receiver;

grasping the free ends of the fastening member legs with said grasping and guiding means;

removing said grasping and guiding means with the fastening member legs attached thereto through said tissue;

and through the openings in the receiver whereby the fastening member legs are retained by said receiver 6. A method according to claim 5 wherein the fastening member is a U-shape staple and the receiver has a pair of openings for accepting and retaining the legs of the staple.

7. A method according to claim 5 wherein said grasping and guiding means have sharpened ends to aid in penetrating tissue.

8. A method according to claim 5 or 6 wherein the grasping means comprises suction applied to the fastening member legs.

9. An instrument for use in joining mammalian tissue with two piece fasteners comprising a fastening member having a plurality of legs joined together at one of the ends thereof with the free ends of said legs adapted to pass through the tissue to be joined and a receiver having a plurality of openings to retain said fastening member legs comprising:

means for holding said fastening member on one side of the tissue to be joined with the legs of said member disposed so as to be able to pass through the tissue to be joined;

means for holding said receiver on the opposite side of the tissue to be joined with the openings in the receiver disposed so as to accept the legs of the fastening member;

means for penetrating the tissue through the openings in the receiver and engaging the free ends of the legs of the fastening member; and means for moving said legs of the fastening member through the tissue and at least partially into the openings in the receiver to be retained thereby.

10. An instrument according to claim 9 wherein means for penetrating the tissue comprises a plurality of hollow leg members having their free ends sharpened to aid in the penetration of the tissue.

11. An instrument according to claim 10 wherein the means for engaging the legs of the fastening member through the tissue is suction supplied through the hollow leg members of the penetrating means.

* * * * *